(12) United States Patent
Feuerstein et al.

(10) Patent No.: US 6,384,069 B1
(45) Date of Patent: May 7, 2002

(54) POSITION-4 SUBSTITUTED 2-PYRROLIDINONE DERIVATIVES TO REDUCE THE LEVEL OF EXTRACELLULAR GLUTAMATE

(75) Inventors: Thomas J. Feuerstein, Horben; Rainer Knoerle, Freiburg, both of (DE)

(73) Assignee: Klinikum der Albert-Ludwigs-Universitaet, Freiburg (DE)

( * ) Notice: Subject to any disclaimer, the term of this patent is extended or adjusted under 35 U.S.C. 154(b) by 0 days.

(21) Appl. No.: 09/554,587

(22) PCT Filed: Nov. 17, 1998

(86) PCT No.: PCT/EP98/07383

§ 371 Date: Jul. 12, 2000

§ 102(e) Date: Jul. 12, 2000

(87) PCT Pub. No.: WO99/25683

PCT Pub. Date: May 27, 1999

(30) Foreign Application Priority Data

Nov. 18, 1997 (DE) .......................... 197 51 062

(51) Int. Cl.$^7$ .................. A61K 31/4015; C07D 207/06; C07D 209/54
(52) U.S. Cl. ....................... 514/409; 514/424; 548/408; 548/543
(58) Field of Search ................................ 514/409, 424; 548/408, 543

(56) References Cited

U.S. PATENT DOCUMENTS

| 4,855,444 A | * 8/1989 | Wambach | ................. 548/408 |
|---|---|---|---|
| 5,319,135 A | 6/1994 | Jennings et al. | ............ 562/507 |

FOREIGN PATENT DOCUMENTS

| EP | 0 414 263 | 2/1991 |
|---|---|---|
| EP | 0 446 570 | 9/1991 |
| WO | WO 97/29101 | 8/1997 |
| WO | WO 97/33858 | 9/1997 |
| WO | WO 97/33859 | 9/1997 |

OTHER PUBLICATIONS

Enders, A. et al., "Pharmacology of a new group of centrally stimulating drugs", *Arzneimittel–Forschung*, pp. 243–250, 1960.

Nakamura, J. et al., "Comparative Studies on the Anticonvulsant Activity of Lipophilic Derivatives of y–Aminobutyric Acid and 2–Pyrrolidinone in Mice", *J. Pharmacobio–Dyn.*, 14, pp. 1–8, 1991.

Reedy, P.A., et al., "3,3–Dialkyl–and 3–Alkyl–3–Benzyl–Substituted 2–Pyrrolidinones: A New Class of Anticonvulsant Agents", *J. Med. Chem.*, 39, pp. 1898–1906, 1996.

Perez de la Mora, M. et al., "Anticonvulsant effect of 5–ethyl, 5–phenyl, 2–pyrrolidinone and its possible relationship to y–aminobutyric acid–dependent inhibitory mechanisms", *Biochemical Pharmacology*, vol. 22, pp. 2635–2639, 1973.

Waldmeier, P.C., et al., "Effect of carbamazepine, oxcarbazepine and lamotrigine on the increase in extracellular glutamate elicited by veratridine in rat cortex and striatum", *Naunyn Schmiedeberg's Arch Pharmacol*, 354, pp. 164–172, 1996.

Sarbbani: Sahay Guha Sircab, "The Preparation of the Substituted Butyrolaccams", *J. Ind. Chem.*, 5, p. 552, 1928.

Siesjo, B.K., et al., "Calcium, Excitotoxins, and Neuronal Death in the Brain", *Annals NY Acad Sci*, 568, pp. 234–251, 1989.

Liu, H.T., et al., "NMDA–receptor regulation of substance P release from primary afferent nociceptors", *Nature*, 386, pp. 721–724, 1997.

Bryson, H.M., et al., "Riluzole A Review of its Pharmacodynamic and Pharmacokinetic Properties and Therapeutic Potential in Amyotrophic Lateral Sclerosis", *Drug Evaluation*, 52, pp. 549–563, 1996.

\* cited by examiner

*Primary Examiner*—T. A. Solola
*Assistant Examiner*—Sonya Wright
(74) *Attorney, Agent, or Firm*—Heller Ehrman White and McAuliffe

(57) ABSTRACT

2-Pyrrolidinone derivatives substituted in position 4 are provided according to the invention for use as therapeutic active ingredient. It has been found, surprisingly, that these compounds are able markedly to reduce the extracellular glutamate level, and the compounds are therefore suitable for the prophylaxis and treatment of a large number of disorders, in particular, stroke.

24 Claims, No Drawings

POSITION-4 SUBSTITUTED 2-PYRROLIDINONE DERIVATIVES TO REDUCE THE LEVEL OF EXTRACELLULAR GLUTAMATE

This application is a 371 of PCT/EP98/07383 filed Nov. 17, 1998.

Glutamate (Glu) is the essential excitatory transmitter in the central nervous system. High extracellular concentrations of Glu in the extracellular space lead to excitotoxic damage (Siesjö B K, Bengtsson F, Grampp W, Theander S, 1989, Calcium, excitotoxins, and neuronal death in the brain. Ann N Y Acad Sci 568:234–251). Examples of disorders of the central nervous system in which excitotoxicity is involved are stroke, hypoglycemia, hypoxia, trauma and epilepsy as acute disturbances, but also chronic disturbances in the sense of neurodegeneration such as Alzheimer's disease, AIDS-associated dementia, amyotrophic lateral sclerosis, Parkinson's disease, chronic alcoholism and others. In cases of chronic pain, an increased glutamatergic transmission (associated with elevated extracellular Glu concentrations) is responsible for plastic changes and is essentially involved in the pathogenesis of the "pain disorder" which is remote from the actual cause (Liu H T, Mantyh P W, Basbaum A I, 1997, NMDA-receptor regulation of substance P release from primary afferent nociceptors. Nature 386:721–724).

Substances which prevent the excitotoxicity of and the plastic changes due to Glu by reducing the extracellular Glu level would be a crucial advantage for the therapy and prophylaxis of the pathological states mentioned.

Several substances which (allegedly) influence glutamatergic transmission are known or already on the market as medicines. They include the Glu-release inhibitor riluzole (Bryson H M, Fulton B, Benfield P, 1996, Riluzole. A review of its pharmacodynamic and pharmacokinetic properties and therapeutic potential in amyotrophic lateral sclerosis. Drugs 52:549–563) and lamotrigine. However, the latter does not, despite assertions to the contrary originally, act as a specific inhibitor of Glu release (Waldmeier P C, Martin P, Stocklin K, Portet C, Schmutz M, 1996, Effect of carbamazepine, oxcarbazepine and lamotrigine on the increase in extracellular glutamate elicited by veratridine in rat cortex and striatum. Naunyn Schmiedeberg's Arch Pharmacol 354:164–172). The GABA derivative gabapentin is also said to inhibit Glu synthesis in the millimolar concentration range (Goldlust A, Su T Z, Welty D F, Taylor C P, Oxender D L, 1995, Effects of anticonvulsant drug gabapentin on the enzymes in metabolic pathways of glutamate and GABA. Epilepsy Res 22:1–11); however, these concentrations cannot be reached in vivo.

Some 1-, 3- and 5-substituted derivatives of 2-pyrrolidinone are known as substances having anticonvulsant activity and/or possibly influencing glutamatergic transmission (Nakamura J, Miwa T, Mori Y, Sasaki H, Shibasaki J, 1991, Comparative studies on the anticonvulsant activity of lipophilic derivatives of gamma-aminobutyric acid and 2-pyrrolidinone in mice. J Pharmacobiodyn 14:1–8; Reddy P A, Hsiang B C, Latifi T N, Hill M W, Woodward K E, Rothman S M, Ferrendelli J A, Covey D F, 1996, 3,3-Dialkyl- and 3-alkyl-3-benzyl-substituted 2-pyrrolidinones: a new class of anticonvulsant agents. J Med Chem 39:1898–1906; De la Mora M P, Tapia R, 1973, Anticonvulsant effect of 5-ethyl,5-phenyl,2-pyrrolidinone and its possible relationship to γ-aminobutyric acid-dependent inhibitory mechanisms. Biochem Pharmacol 22:2635–2639).

The publication Arzneimittelforschung 10, 1960, page 243–250 discloses in Table I No. XVII the compound

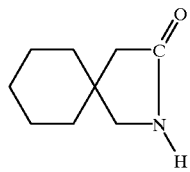

However, this compound is not regarded as particularly active, as is evident from the discussion in the right-hand column on page 249 of this publication. Nor does the publication contain any reference to the use of this compound as pharmaceutical.

At present there is no satisfactory pharmaceutical which effectively reduces the extracellular glutamate level. Even the medicines riluzole and lamotrigine, which are already commercially available, have only low activity as inhibitors of Glu release and show side effects, through metabolism or their mechanism of action, which restricts their therapeutic use.

It is therefore an object of the invention to provide novel medicinal substances and pharmaceuticals which are effective for disorders which are attributable to an elevated glutamate level and which can therefore be employed for the prophylaxis and treatment of disorders of the central nervous system such as stroke, hypoglycemia, hypoxia, trauma and epilepsy, Alzheimer's disease, AIDS-associated dementia, amyotrophic lateral sclerosis, Parkinson's disease and chronic alcoholism. It is intended that these novel pharmaceuticals not have the disadvantages of the pharmaceuticals disclosed in the prior art.

The pharmaceuticals are preferably able to influence glutamatergic transmission and reduce the extracellular glutamate level and/or prevent the depolarization and overexcitation of postsynaptic cells, for example by presynaptically released glutamate.

This object is achieved according to the invention by providing a 2-pyrrolidinone derivative of the general formula

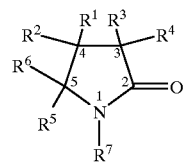

in which $R^1$ and $R^2$ are, independently of one another, hydrogen atoms, hydroxyl groups, amino groups, $C_1$–$C_{10}$ alkoxy radicals, $C_1$–$C_{10}$ alkyl radicals or $C_1$–$C_{10}$ alkylamino radicals, or $R^1$ and $R^2$ together with the carbon atom in position 4 of the pyrrolidinone ring form a five- to ten-membered saturated or unsaturated ring which, besides carbon atoms, may have up to 2 heteroatoms selected from oxygen, sulfur and nitrogen atoms, and which is unsubstituted or is substituted by up to 3 substituents selected from hydroxyl groups, amino groups, $C_1$–$C_4$ alkyl radicals, $C_1$–$C_4$ alkoxy radicals and $C_1$–$C_4$ alkylamino radicals, with the proviso that $R^1$ and $R^2$ are not both hydrogen atoms, $R^3$, $R^4$, $R^5$ and $R^6$ are, each independently of one another, hydrogen atoms, halogen atoms, hydroxyl groups, amino groups, $C_1$–$C_{10}$ alkyl radicals, $C_1$–$C_{10}$ alkoxy radicals, $C_1$–$C_{10}$ alkylamino radicals or $C_6$–$C_{10}$ aryl radicals, and $R^7$ is a hydrogen atom or a $C_1$–$C_{10}$ alkyl radical or $C_1$–$C_{10}$ acyl radical, pharmacologically acceptable salts thereof and prodrugs thereof for use as therapeutic active ingredient.

The alkyl radicals as well as the alkyl constituents of the alkoxy radicals and alkylamino radicals may be straight-chain or branched.

It has been found, surprisingly, that 2-pyrrolidinone derivatives which have in position 4 at least one substituent as defined above have an excellent effect in reducing the extracellular glutamate level and can therefore be used for the prophylaxis and treatment of disorders of the central nervous system such as stroke, hypoglycemia, hypoxia, trauma and epilepsy, Alzheimer's disease, AIDS-associated dementia, amyotrophic lateral sclerosis, Parkinson's disease and chronic alcoholism. The compounds may likewise preferentially prevent depolarization and over-excitation of postsynaptic cells, for example by presynaptically released glutamate. Substitution of the 2-pyrrolidinone derivatives according to the invention in positions 3 and 5 of the pyrrolidinone ring is substantially uncritical as long as substitution in position 4 of the pyrrolidinone ring is ensured. Preferred 2-pyrrolidinone derivatives are unsubstituted in positions 3 and 5 or have one or two alkyl substituents with up to 10 carbon atoms, preferably up to 6 carbon atoms and/or one or two aryl substituents with 6 to 10 carbon atoms, preferably phenyl groups.

Substitution on the nitrogen atom of the 2-pyrrolidinone derivatives is also substantially uncritical, but the nitrogen atom of the 2-pyrrolidinone derivatives according to the invention is preferably unsubstituted or substituted by a $C_1$–$C_6$ alkyl radical or a $C_1$–$C_6$ acyl radical.

The substitution at position 4 of the pyrrolidinone ring is essential for the 2-pyrrolidinone derivatives according to the invention. It is therefore necessary for at least one of the radicals $R^1$ and $R^2$ to be different from hydrogen. One of the radicals $R^1$ and $R^2$ is preferably a hydrogen atom, and other radical is preferably a $C_1$–$C_{10}$ alkyl radical, particularly preferably a $C_1$–$C_6$ alkyl radical.

If the radicals $R^1$ and $R^2$ are different, as in the particularly preferred embodiment of the invention described above, the claimed 2-pyrrolidinone derivatives show optical isomerism. The invention relates both to the pure R and to the pure S form of the pyrrolidinone derivatives, but also to any racemic mixtures of the R and S forms.

It is particularly preferred according to the invention for the radicals $R^1$ and $R^2$ to form, together with the carbon atom in position 4 of the pyrrolidinone ring, a saturated or unsaturated 5- to 10-membered ring. This ring may have up to two heteroatoms selected from oxygen, sulfur and nitrogen atoms and be unsubstituted or substituted by up to three substituents selected from hydroxyl groups, amino groups, $C_1$–$C_4$ alkyl radicals, $C_1$–$C_4$ alkoxy radicals and $C_1$–$C_4$ alkylamino radicals. However, the radicals $R^1$ and $R^2$ preferably form an unsubstituted ring which preferably has no heteroatoms, is preferably saturated and particularly preferably consists of six carbon atoms, including the carbon atom in position 4 of the 2-pyrrolidinone ring. A particularly preferred 2-pyrrolidinone derivative of the invention is 8-azaspiro[5,4]decan-9-one (gabapentin lactam).

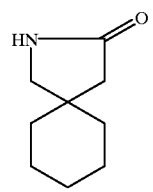

Where at least one of the radicals $R^3$, $R^4$, $R^5$ and $R^6$ is different from hydrogen, structural isomers also occur in addition to the optical isomers (to which the invention relates). All structural isomers and their mixtures are included among the 2-pyrrolidinone derivatives according to the invention.

Instead of the 2-pyrrolidinone derivative as defined above, it is also possible to use pharmacologically acceptable salts, in particular acid addition salts, of the 2-pyrrolidinone derivative. It is likewise possible to use a pharmaceutical precursor (prodrug) of the 2-pyrrolidinone derivatives according to the invention as therapeutic active ingredient. Such a prodrug means a compound which is not itself pharmacologically active but which is converted after administration to a patient in vivo into an active 2-pyrrolidinone derivative as defined above.

The compounds according to the invention can be prepared in a manner known per se. Thus, the 8-azaspiro[5,4]decan-9-one which is particularly preferred according to the invention is already described in the literature (Kearney A. S., Mehta S. C., Radebaugh G. W., The effect of cyclodextrins on the rate of intramolecular lactamization of gabapentin in aqueous solution. International Journal of Pharmaceutics, 78 (1992), 25–34, and the reference, which has already been discussed above, Arzneimittelforschung 10, 1960, pages 243–250), but there is no proposal that this compound be used as therapeutic active ingredient. The 8-azaspiro[5,4]decan-9-one which is preferred according to the invention can be regarded as lactam of the known compound gabapentin and be prepared, for example, by irradiation of a phosphate-buffered aqueous gabapentin solution with ultraviolet light. Substituted derivatives of 8-azaspiro[5,4]decan-9-one can be prepared by lactamization of appropriately substituted gabapentin derivatives. Preferred derivatives are those having a $C_1$–$C_4$ alkyl radical, a halogen, a hydroxyl group or an amino group, preferably a $C_1$–$C_4$ alkyl radical or a halogen atom.

The compound can also be prepared in accordance with the following scheme.

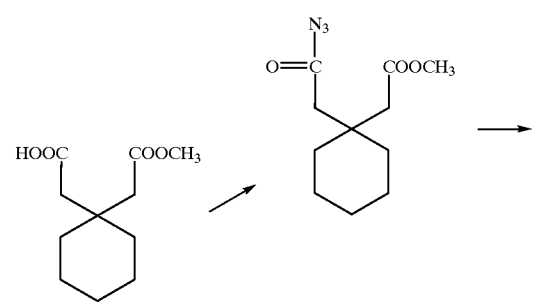

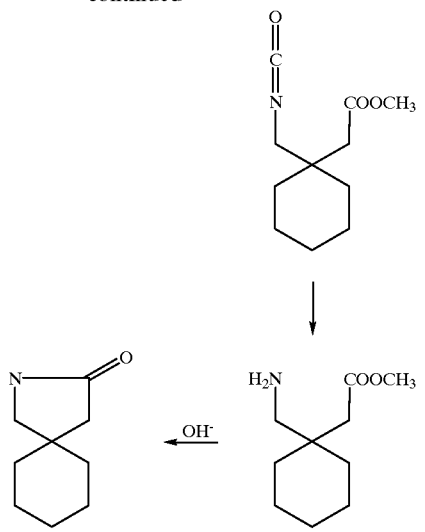

1,1-Cyclohexanediacetic acid monomethyl ester is converted via the corresponding acid chloride into the azide. The azide is degraded by the Curtius method to the isocyanate. The isocyanate is then hydrolyzed to give methyl 1-aminomethyl-1-cyclohexaneacetate. Heating this substance in alkaline methanol under reflux for three days affords 8-azaspiro[5,4]decan-9-one or gabapentin lactam.

A general synthetic method for the 4-substituted 2-pyrrolidinones according to the invention starts, based on the synthesis of 3-substituted GABA derivatives published by Andruszkiewicz and Silverman (R. Andruszkiewicz and R. B. Silverman, Synthesis 953–955 (1989)) from appropriately substituted α, β-unsaturated carboxylic esters (1) which can be obtained inter alia by a Reformatzky reaction. After reaction with nitromethane, a Michael addition results in a nitro compound (2) which is converted by reduction with elemental hydrogen into the corresponding amino compound (3). After ester cleavage and activation of the carboxylate function by a good leaving group (for example conversion into the carbonyl halide), the corresponding 4-substituted 2-pyrrolidinone is obtained by cyclization.

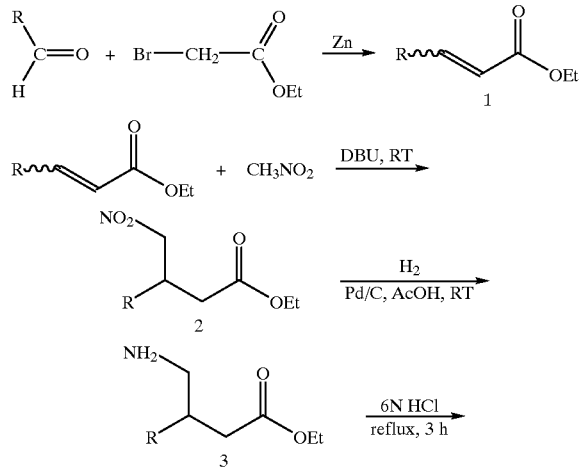

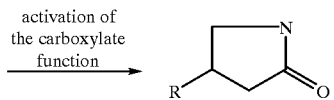

The compositions according to the invention can be formulated in a manner known per se to give the pharmaceuticals for mammals, preferably humans. The compositions according to the invention are present in the pharmaceuticals mixed with an organic or inorganic pharmaceutical carrier suitable for enteral or parenteral administrations. Oral administration of the compositions according to the invention by way of tablets, capsules, powders or in liquid form, such as suspensions, in solution, as emulsion or as syrup is particularly preferred.

When formulated as tablets, conventional pharmaceutical carriers are used, such as sodium citrate, lactose, microcrystalline cellulose and starch, lubricants such as anhydrous silica, hydrogenated castor oil, magnesium stearate, sodium lauryl sulfate and talc, and binders such as starch paste, glucose, lactose, gum arabic, mannitol, magnesium trisilicate and talc. If the compositions according to the invention are to be administered by way of liquids it is possible to use conventional liquid carriers.

Formulation for injections and infusions or as suppositories is likewise possible, as is known in the specialist area and described in relevant standard works.

The compositions according to the invention can likewise be formulated in a manner known per se as depot formulations or to give pharmaceuticals with delayed or retarded release.

The dose form of the compositions according to the invention depends on the specific composition and other factors and can be determined by a skilled worker on the basis of the condition of the patient to be treated, the severity and nature of the disease to be treated, possible side effects of the compounds etc.

The examples illustrate the invention.

EXAMPLE 1

A solution of gabapentin (100 μM) in physiological buffer (composition below) with a pH of 7.4 was prepared and irradiated with ultraviolet light (260 and 330 nanometers) at 37° C. for two hours. As described in Kearney A. S. et al., International Journal of Pharmaceutics, 78 (1992), 25–34, this slowly produces the lactam 8-azaspiro[5,4]decan-9-one. Because of the slow reaction rate, a yield of about 1% is assumed in accordance with Kearney et al. (1992), which corresponds to a 1 μM solution.

The activity of this solution in reducing the extracellular glutamate level was shown by means of superfusion experiments on rat brain slices. Slices with a thickness of 350 μm from the rat striatum were used for this. In each case, two slices were employed in a superfusion chamber with an extremely small dead volume, about 100 μl. Physiological buffer (concentrations in mM: NaCl 121, KCl 1.8, CaCl$_2$ 1.3, MgSO$_4$ 1.2, NaHCO$_3$ 25, KH$_2$PO$_4$ 1.2, glucose 11, pH 7.4, 95% O$_2$/5% CO$_2$-saturated) is then passed over them at 37° C. After a preliminary perfusion, which serves in particular to remove tissue particles and amino acids released by the injury to the tissue, superfusate fractions are collected at a flow rate of 400 to 800 μl every five minutes. Six of the 12 chambers available are continuously flushed from the start of the preliminary perfusion with an approximately 1 μM solution of 8-azaspiro[5,4]decan-9-one, and the remaining chambers which are flushed with buffer serve as control. The superfusates obtained are filtered (0.45 µm pore size) and the amino acid concentrations are determined by HPLC. Details of the method are described, for example, in R. Knörle et al., Neuroscience Letters 221 (1997), 169–172.

The results show a marked reduction in the extracellular glutamate concentration due to the 8-azaspiro[5,4]decan-9-one. With the samples containing the compound according to the invention, 0.12 µM glutamate, $CI_{95}=[0.10, 0.13]$ was found, whereas in the control tests 0.24 µM glutamate, $CI_{95}=[0.19, 0.29]$ was found.

EXAMPLE 2

The neuroprotective effect of the compounds according to the invention was demonstrated in vivo on the basis of the publication in Invest Ophthalmol Vis Sci 39: 1063–1066, 1998. The following results were found:

10 rats were treated with 0.9% NaCl i.p. at the start of a unilateral one-hour intraocular pressure increase. After 6 hours, the treatment was again carried out with 0.9% NaCl i.p. After 14 days, the rats were sacrificed, and the retinal gangliocytes were investigated. Compared with the respective control eye, only 17.4% (±4%) of the retinal gangliocytes had survived. The rats behaved completely normally in the 14 days after the test, and no animal died.

In the test group, likewise of 10 rats, 50 mg/kg 8-azaspiro[5,4]decan-9-one was administered i.p. at the start of a unilateral one-hour intraocular pressure increase. The compound was administered again in a dose of 50 mg/kg 6 hours after the intraocular pressure increase. After 14 days, the rats were sacrificed, and the retinal gangliocytes were investigated. It emerged that, compared with the respective control eye, 35% (±7%) of the retinal gangliocytes survived. The rats behaved completely normally in the 14 days after the test, and no animal died.

This test clearly shows the increase in the surviving retinal gangliocytes after pressure-induced retinal ischemia from 17.4% (±4%) to 35.0% (±7%). The neurodegeneration in this glaucoma model is based on an NMDA receptor-mediated Glu toxicity.

EXAMPLE 3

It was possible to show in another in vitro test that the antiischemic mechanism of action of the compounds according to the invention is based on a reduction in the released Glu.

Rat hippocampus slices 350 µm thick were incubated in 3 ml of medium at 37° C. for 60 minutes. The medium contained 2 µM [$^3$H]-Gln to label the endogenous Gln pool. The slices then synthesized Glu. The slices were washed and then exposed to superfusion with a buffer for 50 minutes. At 5-minute intervals, [$^3$H]-Glu was extracted by anion exchange chromatography from a total of 15 superfusion samples and was measured by liquid scintillation counting. The fractional rates of [$^3$H]-Glu release were calculated from the [$^3$H]-Glu extracted from the superfusion samples and from the tissue slices after the superfusion.

Gabapentin lactam was first investigated in a model in which the release was induced by electrical stimulation. The release in this model responds both to tetrodotoxin and to extracellular $Ca^{++}$ ions. After the incubation with tritiated Gln, the slices were exposed to a superfusion and electrically stimulated twice, employing 540 pulses of 4 ms, 6 Hz and 60 mA. The superfusion was carried out at room temperature, not at 37° C. In addition, 100 µM of the Glu uptake blocker PDC was present so that renewed uptake of released Glu is reduced. TTX or gabapentin lactam was added from 15 minutes before the second stimulation onward. It was found that electrically induced release of Glu is partly inhibited by TTX, but not by gabapentin lactam. The quasiphysiological release of Glu is therefore not influenced by gabapentin lactam.

The model of endogenously produced [$^3$H]-Glu was likewise used to generate ischemic conditions in vitro. To make a slice "quasiischemic", oxygen and glucose were replaced by nitrogen and sucrose during the superfusion. Sucrose was used in place of 11 mM glucose in order to maintain the osmolarity of the superfusion fluid. It is known that sucrose cannot be cleaved in vitro to glucose and fructose. Unlike the tests in which the [$^3$H]-Glu release was induced electrically, and in order to simulate an ischemia as well as possible, the [$^3$H]-Glu release was carried out during the incubation and superfusion at 37° C. It was found that the usual high concentration of the Glu uptake inhibitor PDC, namely 100 µM, noticeably reduced the response to the ischemia. All the tests were therefore carried out in the presence of only 3 µM PDC, which markedly increased the effect of the ischemia.

It was found that in this in vitro ischemia model, gabapentin lactam reduces the neurotoxic [3H]-Glu output significantly.

The compounds thus unambiguously prevent in vitro the large increase in extracellular tritium-Glu in rat hippocampus slices (previously loaded with tritium-glutamine) after replacement of $O_2$ by $N_2$ and of glucose by sucrose, specifically by about 50%. The quasiphysiological action potential-mediated Glu release was, however, unaffected by gabapentin lactam.

Comparative Example 1

Example 1 was repeated with the modification that the gabapentin-containing solution was not irradiated with ultraviolet light but was used directly in the test. The comparative solution thus contains exclusively gabapentin but no 8-azaspiro[5,4]decan-9-one. In the corresponding tests, no difference could be found between the samples treated with the gabapentin solution and the comparative samples.

Comparative Example 2

Example 2 above was repeated but employed instead of 8-azaspiro[5,4]decan-9-one the structurally similar compound gabapentin. It emerged that gabapentin showed no protective effect whatever against neuro-degeneration in this glaucoma model.

What is claimed is:

1. A method of treating disorders caused by an elevated extracellular glutamate level, wherein the disorder is selected from the group consisting of stroke, chronic pain, hypoglycemia, hypoxia, trauma, Alzheimer's disease, AIDS-associated dementia, amyotrophic lateral sclerosis, Parkinson's disease, and chronic alcoholism, comprising administering to a patient in need thereof a pharmaceutical composition comprising a pharmaceutically acceptable carrier and a pharmaceutically effective amount of a 2-pyrrolidinone derivative of the general formula:

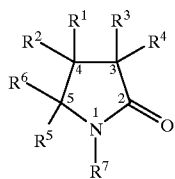

in which
  $R^1$ and $R^2$ are, independently of one another, hydrogen atoms, hydroxyl groups, amino groups, $C_1$–$C_{10}$ alkoxy radicals, $C_1$–$C_{10}$ alkyl radicals or $C_1$–$C_{10}$ alkyl-amino radicals, or $R^1$ and $R^2$ together with the carbon atom in position 4 of the pyrrolidinone ring form a five- to ten-membered saturated or unsaturated ring which, besides carbon atoms, may have up to 2 heteroatoms selected from oxygen, sulfur and nitrogen atoms, and which is unsubstituted or is substituted by up to 3 substituents selected from hydroxyl groups, amino groups, $C_1$–$C_4$ alkyl radicals, $C_1$–$C_4$ alkoxy radicals and $C_1$–$C_4$ alkylamino radicals, with the proviso that $R^1$ and $R^2$ are not both hydrogen atoms,
  $R^3$, $R^4$, $R^5$ and $R^6$ are, each independently of one another, hydrogen atoms, halogen atoms, hydroxyl groups, amino groups, $C_1$–$C_{10}$ alkyl radicals, $C_1$–$C_{10}$ alkoxy radicals, $C_1$–$C_{10}$ alkylamino radicals or $C_6$–$C_{10}$ aryl radicals, and
  $R^7$ is a hydrogen atom or a $C_1$–$C_{10}$ aryl radical or $C_1$–$C_{10}$ acyl radical,
or a pharmacologically acceptable salt thereof.

2. The method of claim 1, wherein in the pyrrolidinone derivative, the radicals $R^3$, $R^4$, $R^5$ and $R^6$ are hydrogen atoms.

3. The method of claim 1, wherein in the 2-pyrrolidinone derivative, one of the radicals $R^1$ and $R^2$ is a hydrogen atom, and the other radical is a $C_1$–$C_{10}$ alkyl radical.

4. The method of claim 1, wherein in the 2-pyrrolidinone derivative of claim 1, the radicals $R^1$ and $R^2$ form, together with the carbon atom in position 4 of the pyrrolidinone ring, a six-membered saturated hydrocarbon ring.

5. A method of treating stroke comprising, administering to a subject a pharmaceutical composition comprising a pharmaceutically acceptable carrier and a pharmaceutically effective amount of a 2-pyrrolidinone derivative of the general formula:

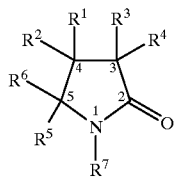

in which
  $R^1$ and $R^2$ are, independently of one another, hydrogen atoms, hydroxyl groups, amino groups, $C_1$–$C_{10}$ alkoxy radicals, $C_1$–$C_{10}$ alkyl radicals or $C_1$–$C_{10}$ alkyl-amino radicals, or $R^1$ and $R^2$ together with the carbon atom in position 4 of the pyrrolidinone ring form a five- to ten-membered saturated or unsaturated ring which, besides carbon atoms, may have up to 2 heteroatoms selected from oxygen, sulfur and nitrogen atoms, and which is unsubstituted or is substituted by up to 3 substituents selected from hydroxyl groups, amino groups, $C_1$–$C_4$ alkyl radicals, $C_1$–$C_4$ alkoxy radicals and $C_1$–$C_4$ alkylamino radicals, with the proviso that $R^1$ and $R^2$ are not both hydrogen atoms,
  $R^3$, $R^4$, $R^5$ and $R^6$ are, each independently of one another, hydrogen atoms, halogen atoms, hydroxyl groups, amino groups, $C_1$–$C_{10}$ alkyl radicals, $C_1$–$C_{10}$ alkoxy radicals, $C_1$–$C_{10}$ alkylamino radicals or $C_6$–$C_{10}$ aryl radicals, and
  $R^7$ is a hydrogen atom or a $C_1$–$C_{10}$ aryl radical or $C_1$–$C_{10}$ acyl radical,
or a pharmacologically acceptable salt thereof.

6. The method of claim 4, wherein said 2-pyrrolidinone derivative comprises 8-azaspiro[5,4] decan-9-one.

7. The method of claim 5, wherein in the pyrrolidinone derivative, the radicals $R^3$, $R^4$, $R^5$ and $R^6$ are hydrogen atoms.

8. The method of claim 5, wherein in the 2-pyrrolidinone derivative, one of the radicals $R^1$ and $R^2$ is a hydrogen atom, and the other radical is a $C_1$–$C_{10}$ alkyl radical.

9. The method of claim 5, wherein in the 2-pyrrolidinone derivative, the radicals $R^1$ and $R^2$ form, together with the carbon atom in position 4 of the pyrrolidinone ring, a six-membered saturated hydrocarbon ring.

10. The method of claim 5, wherein said 2-pyrrolidinone derivative comprises 8-azaspiro[5,4] decan-9-one.

11. A method of reducing the concentration of extracellular glutamate in a patient comprising, administering to a subject a pharmaceutical composition comprising a pharmaceutically acceptable carrier and a pharmaceutically effective amount of a 2-pyrrolidinone derivative of the general formula:

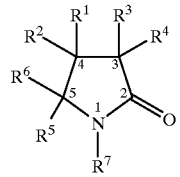

in which
  $R^1$ and $R^2$ are, independently of one another, hydrogen atoms, hydroxyl groups, amino groups, $C_1$–$C_{10}$ alkoxy radicals, $C_1$–$C_{10}$ alkyl radicals or $C_1$–$C_{10}$ alkyl-amino radicals, or $R^1$ and $R^2$ together with the carbon atom in position 4 of the pyrrolidinone ring form a five- to ten-membered saturated or unsaturated ring which, besides carbon atoms, may have up to 2 heteroatoms selected from oxygen, sulfur and nitrogen atoms, and which is unsubstituted or is substituted by up to 3 substituents selected from hydroxyl groups, amino groups, $C_1$–$C_4$ alkyl radicals, $C_1$–$C_4$ alkoxy radicals and $C_1$–$C_4$ alkylamino radicals, with the proviso that $R^1$ and $R^2$ are not both hydrogen atoms,
  $R^3$, $R^4$, $R^5$ and $R^6$ are, each independently of one another, hydrogen atoms, halogen atoms, hydroxyl groups, amino groups, $C_1$–$C_{10}$ alkyl radicals, $C_1$–$C_{10}$ alkoxy radicals, $C_1$–$C_{10}$ alkylamino radicals or $C_6$–$C_{10}$ aryl radicals, and
  $R^7$ is a hydrogen atom or a $C_1$–$C_{10}$ aryl radical or $C_1$–$C_{10}$ acyl radical,
or a pharmacologically acceptable salt thereof.

12. The method of claim 11, wherein in the pyrrolidinone derivative, the radicals $R^3$, $R^4$, $R^5$ and $R^6$ are hydrogen atoms.

13. The method of claim 11, wherein in the 2-pyrrolidinone derivative, one of the radicals $R^1$ and $R^2$ is a hydrogen atom, and the other radical is a $C_1$ to $C_{10}$ alkyl radical.

14. The method of claim 11, wherein in the 2-pyrrolidinone derivative, the radicals $R^1$ and $R^2$ form, together with the carbon atom in position 4 of the pyrrolidinone ring, a six-membered saturated hydrocarbon ring.

15. The method of claim 11, wherein said 2-pyrrolidinone derivative comprises 8-azaspiro[5,4] decan-9-one.

16. A method of treating disorders caused by an elevated extracellular glutamate level, wherein the disorder is selected from the group consisting of stroke, chronic pain, hypoglycemia, hypoxia, trauma, Alzheimer's disease, AIDS-associated dementia, amyotrophic lateral sclerosis, Parkinson's disease, epilepsy and chronic alcoholism, comprising administering to a patient in need thereof a pharmaceutical composition comprising a pharmaceutically acceptable carrier and a pharmaceutically effective amount of a 2-pyrrolidinone derivative of the general formula:

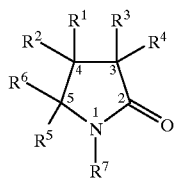

in which $R^1$ and $R^2$ together with the carbon atom in position 4 of the pyrrolidinone ring form a five- to ten-membered saturated or unsaturated ring which, besides carbon atoms, may have up to 2 heteroatoms selected from oxygen, sulfur and nitrogen atoms, and which is unsubstituted or is substituted by up to 3 substituents selected from hydroxyl groups, amino groups, $C_1$–$C_4$ alkyl radicals, $C_1$–$C_4$ alkoxy radicals and $C_1$–$C_4$ alkylamino radicals, $R^3$, $R^4$, $R^5$ and $R^6$ are, each independently of one another, hydrogen atoms, halogen atoms, hydroxyl groups, amino groups, $C_1$–$C_{10}$ alkyl radicals, $C_1$–$C_{10}$ alkoxy radicals, $C_1$–$C_{10}$ alkylamino radicals or $C_6$–$C_{10}$ aryl radicals, and $R^7$ is a hydrogen atom or a $C_1$–$C_{10}$ aryl radical or $C_1$–$C_{10}$ acyl radical, or a pharmacologically acceptable salt thereof.

17. The method of claim 16, wherein said 2-pyrrolidinone derivative comprises 8-azaspiro[5,4] decan-9-one.

18. A method of treating stroke comprising, administering to a subject a pharmaceutical composition comprising a pharmaceutically acceptable carrier and a pharmaceutically effective amount of a 2-pyrrolidinone derivative of the general formula:

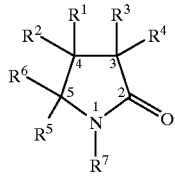

in which $R^1$ and $R^2$ are, independently of one another, hydrogen atoms, hydroxyl groups, amino groups, $C_1$–$C_{10}$ alkoxy radicals, $C_1$–$C_{10}$ alkyl radicals or $C_1$–$C_{10}$ alkyl-amino radicals, or $R^1$ and $R^2$ together with the carbon atom in position 4 of the pyrrolidinone ring form a five- to ten-membered saturated or unsaturated ring which, besides carbon atoms, may have up to 2 heteroatoms selected from oxygen, sulfur and nitrogen atoms, and which is unsubstituted or is substituted by up to 3 substituents selected from hydroxyl groups, amino groups, $C_1$–$C_4$ alkyl radicals, $C_1$–$C_4$ alkoxy radicals and $C_1$–$C_4$ alkylamino radicals, with the proviso that $R^1$ and $R^2$ are not both hydrogen atoms, $R^3$, $R^4$, $R^5$ and $R^6$ are each hydrogen atoms, $R^7$ is a hydrogen atom or a $C_1$–$C_{10}$ aryl radical or $C_1$–$C_{10}$ acyl radical, or a pharmacologically acceptable salt thereof.

19. The method of claim 18, wherein in the 2-pyrrolidinone derivative, one of the radicals $R^1$ and $R^2$ is a hydrogen atom, and the other radical is a $C_1$–$C_{10}$ alkyl radical.

20. The method of claim 18, wherein in the 2-pyrrolidinone derivative, the radicals $R^1$ and $R^2$ form, together with the carbon atom in position 4 of the pyrrolidinone ring, a six-membered saturated hydrocarbon ring.

21. The method of claim 18, wherein said 2-pyrrolidinone derivative comprises 8-azaspiro[5,4] decan-9-one.

22. A method of reducing the concentration of extracellular glutamate in a patient comprising, administering to a subject a pharmaceutical composition comprising a pharmaceutically acceptable carrier and a pharmaceutically effective amount of a 2-pyrrolidinone derivative of the general formula

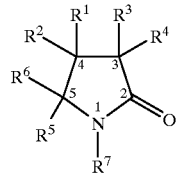

in which $R^1$ and $R^2$ together with the carbon atom in position 4 of the pyrrolidinone ring form a five- to ten-membered saturated or unsaturated ring which, besides carbon atoms, may have up to 2 heteroatoms selected from oxygen, sulfur and nitrogen atoms, and which is unsubstituted or is substituted by up to 3 substituents selected from hydroxyl group, amino groups, $C_1$–$C_4$ alkyl radicals, $C_1$–$C_4$ alkoxy radicals and $C_1$–$C_4$ alkylamino radicals, $R^3$, $R^4$, $R^5$ and $R^6$ are, each independently of one another, hydrogen atoms, halogen atoms, hydroxyl groups, amino groups, $C_1$–$C_{10}$ alkyl radicals, $C_1$–$C_{10}$ alkoxy radicals, $C_1$–$C_{10}$ alkylamino radicals or $C_6$–$C_{10}$ aryl radicals, and $R^7$ is a hydrogen atom or a $C_1$–$C_{10}$ aryl radical or $C_1$–$C_{10}$ acyl radical, or a pharmacologically acceptable salt thereof.

23. The method of claim 22, wherein in the 2-pyrrolidinone derivative, the radicals $R^1$ and $R^2$ form, together with the carbon atom in position 4 of the pyrrolidinone ring, a six-membered saturated hydrocarbon ring.

24. The method of claim 22, wherein said 2-pyrrolidinone derivative comprises 8-azaspiro[5,4] decan-9-one.

* * * * *